United States Patent [19]

Martin

[11] Patent Number: 5,043,333
[45] Date of Patent: * Aug. 27, 1991

[54] ZINC-LYSOCELLING THERAPEUTIC AND GROWTH PROMOTING AGENTS

[75] Inventor: Jerome L. Martin, Terre Haute, Ind.

[73] Assignee: International Minerals & Chemical Corp., Northbrook, Ill.

[*] Notice: The portion of the term of this patent subsequent to Mar. 31, 2004 has been disclaimed.

[21] Appl. No.: 262,138

[22] Filed: Oct. 21, 1988

Related U.S. Application Data

[63] Continuation of Ser. No. 686,617, Dec. 26, 1984, abandoned, which is a continuation of Ser. No. 486,458, Apr. 25, 1983, abandoned, which is a continuation of Ser. No. 139,567, Apr. 11, 1980, abandoned, which is a continuation-in-part of Ser. No. 56,643, Jul. 11, 1979, abandoned.

[51] Int. Cl.$^5$ .............................. A61K 31/555
[52] U.S. Cl. ................................ 514/188; 435/119; 556/118
[58] Field of Search ............... 514/451, 188; 556/118; 435/119

[56] References Cited

U.S. PATENT DOCUMENTS

| | | | |
|---|---|---|---|
| 3,501,568 | 3/1970 | Henry et al. | 424/115 |
| 3,555,150 | 1/1971 | Gorman et al. | 424/122 |
| 3,627,883 | 12/1971 | Gorman | 424/122 |
| 3,705,238 | 12/1972 | Hamill et al. | 424/121 |
| 3,715,372 | 2/1972 | Stempel et al. | 260/345.8 |
| 3,719,753 | 3/1973 | Berger et al. | 424/122 |
| 3,794,732 | 6/1979 | Raun | 424/181 |
| 3,832,358 | 8/1974 | Chamberlin | 260/345.7 |
| 3,839,557 | 10/1974 | Raun | 424/115 |
| 3,857,948 | 12/1974 | Tanaka et al. | 424/283 |
| 3,873,715 | 3/1975 | Pressman et al. | 424/283 |
| 3,923,823 | 12/1975 | Gale et al. | 424/272 X |
| 3,932,619 | 1/1976 | Brannon et al. | 424/120 |
| 3,937,836 | 2/1976 | Raun | 424/283 |
| 3,944,573 | 3/1976 | Westley | 260/347.3 |
| 3,950,514 | 4/1976 | Sawada et al. | 424/121 |
| 3,985,872 | 10/1978 | Chamberlin | 424/122 |
| 3,995,027 | 11/1976 | Gale et al. | 424/115 |
| 4,009,262 | 2/1977 | Boeck et al. | 424/123 |
| 4,016,256 | 4/1977 | Ishida et al. | 424/121 |
| 4,033,823 | 7/1977 | Liu et al. | 195/80 R |
| 4,035,481 | 7/1977 | Berg et al. | 424/122 |
| 4,058,620 | 11/1977 | Westley | 424/283 |
| 4,061,775 | 12/1977 | McDougald | 424/263 |
| 4,066,781 | 1/1978 | Shibuya et al. | 424/283 |
| 4,075,323 | 2/1978 | McDougald | 424/114 |
| 4,076,834 | 2/1978 | Westley | 424/283 |
| 4,083,968 | 4/1978 | Westley | 424/181 |
| 4,110,436 | 8/1978 | Nakasukasa | 424/122 |
| 4,129,578 | 12/1978 | Celmer et al. | 424/283 X |
| 4,129,659 | 12/1978 | Pressman et al. | 424/283 |
| 4,137,241 | 1/1979 | Liu et al. | 260/245.7 R |
| 4,138,496 | 2/1979 | Shibata et al. | 424/283 |
| 4,141,907 | 2/1979 | Nakatsukasa et al. | 260/345.7 R |
| 4,148,890 | 4/1979 | Czok et al. | 424/181 |
| 4,159,322 | 6/1979 | Cloyd | 424/181 |
| 4,161,520 | 7/1979 | Osborne et al. | 424/115 |
| 4,164,586 | 8/1979 | Westley | 424/285 |
| 4,168,272 | 9/1979 | Westley | 260/345.7 R |
| 4,174,404 | 11/1979 | Nakatsukasa et al. | 424/283 |
| 4,192,887 | 3/1980 | Cloyd et al. | 424/283 |
| 4,193,928 | 3/1980 | Coffen | 260/345.7 R |
| 4,218,443 | 8/1980 | Comai et al. | 424/181 |
| 4,305,956 | 12/1981 | Shibuya et al. | 424/283 |
| 4,478,935 | 10/1984 | Williams et al. | |
| 4,654,334 | 3/1987 | Williams et al. | |
| 4,761,426 | 8/1988 | Martin et al. | |

OTHER PUBLICATIONS

*The Journal of Antibiotics*, vol. 28, 118–121 (1975); vol. 29, 692–95(1976); vol. 30, 903–7 (1977); vol. 31, 750–5 (1978); vol. 31, 1–6 (1978).

*Biochemistry*, vol. 15, No. 5, Mar. 9, 1976. 935–43.

*Am. Rev. Biochemistry*, 501–530 (1976).

Westley, *Advances in Applied Microbiology*, 22 177–223 (1977).

Otake et al., *J. S. C. Chem. Comm.*, pp. 92–93 (1975).

L. L. Berger, et al., *J. of Animal Sci.*, vol. 53, No. 6, pp. 1440–1445 (1981).

J. Berger, et al., "Isolation of Three New Crystalline Antibiotics from Streptomyces", Nov. 1951.

J. F. Blount, et al., *Chemical Communications*, pp. 927–928 (1971).

A. H. Caswell et al., *Biochemical and Biophysical Research Communications*, vol. 49, No. 1, pp. 292–298 (1972).

H. Degani, et al., *Biochemistry*, vol. 13, No. 24, pp. 5022–5032 (1974).

T. Fehr, et al., *The Journal of Antibiotics*, vol. XXXII, No. 5, pp. 535–536 (May 1979).

T. Fehr, et al., *The Journal Antibiotics*, vol. XXX, No. 11, pp. 903–907 (Nov. 1977).

P. Gachion et al., *Chemical Communications*, pp. 1421–1422 (1970).

P. Gachion et al., *The Journal of Antibiotics*, vol. XXVIII, No. 5, pp. 345–350 (May 1975).

P. Gachon et al., *The Journal of Antibiotics*, vol. XXVIII, No. 5, pp. 351–357 (May 1975).

P. Gachon et al., *The Journal of Antibiotics*, vol. XXIX, No. 6, pp. 603–610. (Jun. 1976).

A. C. Hammond et al., *Journal of Animal Science*, vol. 51, No. 1, pp. 207–214 (1980).

R. L. Harned et al., *Antibiotics and Chemotherapy*, vol. I, No. 9, pp. 594–596 (Dec. 1951).

A. Imada et al., *The Journal of Antibiotics*, vol. XXXI, No. 1, pp. 7–14 (Jan. 1978).

(List continued on next page.)

*Primary Examiner*—Sam Rosen
*Attorney, Agent, or Firm*—Wendell Ray Guffey; George R. Repper; Thomas L. Farquer

[57] ABSTRACT

A zinc complex of lysocellin is provided. The complex acts as a coccidiostat and growth-promoting agent when administered to poultry.

6 Claims, No Drawings

OTHER PUBLICATIONS

C. Keller-Juslen et al., *The Journal of Antibiotics*, vol. XXXI, No. 9, pp. 820-828 (Sep. 1978).

F. Kitame et al., *The Journal of Antibiotics*, vol. XXVII, No. 11 pp. 884-888 (Nov. 1974).

Y. Myazaki et al., *The Journal of Antibiotics*, vol. XXVII, No. 11 pp. 814-821 (Nov. 1974).

S. Omura et al., *The Journal of Antibiotics*, vol. XXIX, No. 1, pp. 15-20 (Jan. 1976).

M. Ohshima, et al., *The Journal of Antibiotics*, vol. XXIX, No. 4, pp. 354-365 (Apr. 1976).

A. Stempel, et al., *The Journal of Antibiotics*, vol. XXII, No. 8, pp. 384-385 (Aug. 1969).

L. K. Steinrauf et al., *Biochemical and Biophysical Research Communications*, vol. 33, No. 1, pp. 29-31 (1968).

L. K. Steinrauf et al., *Biochemical and Biophysical Research Communications*, vol. 45, No. 5, pp. 1279-1283 (1971).

Merck Index, 9th Edition, No. 6081.

Mitani et al., *The Journal of Antibiotics*, vol. XXXI, No. 9, pp. 888-893 (Sep. 1978).

M. Mitani et al., *The Journal of Antibiotics*, vol. XXX, No. 3, pp. 239-243 (Mar. 1977).

N. Otake, et al., *Agric. Biol. Chem.*, 42 (10), 1879-1886 (1978).

T. G. Nagaraja, et al., *Journal of Animal Science*, vol. 53, No. 1, pp. 206-216 (1981).

ZINC-LYSOCELLING THERAPEUTIC AND GROWTH PROMOTING AGENTS

This application is a continuation of application Ser. No. 686,617, filed Dec. 26, 1984, now abandoned, which was a continuation of application Ser. No. 486,458, filed Apr. 25, 1983, now abandoned, which was a continuation of application Ser. No. 139,567, filed Apr. 11, 1980, now abandoned, which was a continuation in part of application Ser. No. 056,643, filed July 11, 1979, now abandoned.

The present invention relates to zinc complexes of linear monovalent polyether antibiotics and non-nitrogen containing divalent polyether antibiotics as new compositions of matter. The present invention further relates to processes for the administration of zinc complexes of linear monovalent and non-nitrogen containing divalent polyether antibiotics to poultry to promote poultry growth, to enhance poultry feeding efficiency, and/or to combat coccidial infections in poultry. In addition, the present invention relates to feed compositions and feed additive compositions containing zinc complexes of linear monovalent and non-nitrogen containing divalent polyether antibiotics.

The present invention also relates to processes for improving cardiovascular function in animals by administering zinc complexes of polyether antibiotics. The present invention further relates to pharmaceutical compositions including zinc complexes of polyether antibiotics for improving cardiovascular function in animals. The present invention also relates to methods for producing zinc complexes of polyether antibiotics. The present invention also relates to methods for the purification of zinc complexes of polyether antibiotics which are formed in fermentation beers such that the zinc complexes are more suitable for administration to an animal such as a human being.

Polyether antibiotics can be generally characterized as carboxylic acid ionophores which can be produced by culturing Streptomyces type microorganisms. These polyether antibiotics have a basic structure generally consisting essentially of the elements oxygen, hydrogen and carbon and possibly nitrogen and have a molecular weight in the range of about 300 to about 1800, most often from about 400 to about 1200. They have low solubility in water, are generally soluble in low molecular weight alcohols, ethers and ketones, and have at least one, and usually one or two, carboxylic acid groups. A generally comprehensive review of this class of antibiotics is set forth in Westley, *Adv. Appl. Microbiology* 22, 177–223 (1977). As is mentioned therein, at least twenty different polyether antibiotics were known at the time the article was written. Since then, additional polyether antibiotics have been discovered.

In the previously noted publication, Westley classified the known polyether antibiotics into four separate classes based on ability of the particular antibiotic to effect the transport of divalent cations and based on the chemical structure of the particular antibiotic. Using these criteria, Westley defined class 1a as those polyether antibiotics which are monovalent polyethers antibiotics. In addition, the polyether antibiotics of this class have a generally linear configuration, i.e., the carboxylic portion of the polyether molecule is attached either directly or indirectly to a terminal ring structure. They generally include from about four to about six tetrahydropyran and/or -furan structures and up to six total ring structures. Included in class 1a are the polyether antibiotics monensin, laidlomycin, nigericin, grisorixin, salinomycin, narasin, lonomycin, X-206, SY-1, noboritomycins A & B, mutalomycin, and alborixin. For the purpose of clarity, the polyether antibiotics of this class are hereinafter referred to as "linear monovalent polyether antibiotics."

Class 1b of the polyether antibiotics are defined by Westley as monovalent monoglycoside polyether antibiotics. These polyether antibiotics, as the class name suggests, include a glycoside type structure, more specifically, a 2,3,6-tideoxy-4-O-methyl-D-erythrohexapyranose moiety, which is attached to the polyether molecule such that a non-linear type molecule is formed, i.e., the carboxylic portion of the polyether molecule is attached either directly or indirectly to a non-terminal ring structure or the molecule has a side chain ring structure, e.g., a 2,3,6-trideoxy-4-0-methyl-D-erythrohexapyranose moiety. Generally, the polyether antibiotics of this class contain about six or seven tetrahydropyran and/or -furan structures.

Class 2a as defined by Westley is directed to divalent polyether antibiotics. These antibiotics are generally of a generally linear configuration, may contain from about two to about three tetrahydropyran and/or -furan structures, up to about three total ring structures and no nitrogen atoms. Included within class 2a are the antibiotics lasalocid and lysocellin. For the purpose of clarity, the polyether antibiotics of this class are hereinafter referred to as "non-nitrogen containing divalent polyether antibiotics." Class 2b of the polyether antibiotics is directed to divalent pyrrole ethers and thus, in contrast to the antibiotics of the other classes, the class 2b antibiotics contain one or more nitrogen atoms.

As was mentioned above, one of the polyether antibiotics in class 2a as defined by Westley is the lasalocid polyether antibiotic. Lasalocid was discovered by Julius Berger et al. in media fermented with a Streptomyces microorganism isolated from a sample of soil collected at Hyde Park, Massachusetts. [Cf. Berger et al., *J. Amer. Chem. Soc.* 73, 5295-8 (1951)]. Originally this material was known by the code name X-537A, and the generic name "lasalocid" was subsequently assigned to the material. Sometime in the late 1960s, it was found that lasalocid was a coccidiostat that is active against such organisms as *Eimeria tenella*, *Eimeria necatrix*, *Eimeria acervulina*, *Eimeria brunetti*, *Eimeria mivati* and *Eimeria maxima* (Stempel et al., U.S. Pat. No. 3,715,372, issued Feb. 6, 1973). On Oct. 8, 1976, the Food and Drug Administration granted approval for the sale of the sodium salt of lasalcoid as a coccidiostat for chickens. Monensin and nigericin are also polyether antibiotics having coccidiostatic properties. [Cf. *Merck Index*, 9th Ed. (1976) No. 6-81 (monensin); Steinrauf et al., *Biochem. and Biophs. Res. Comm.* 33, 29–31 (1968); Stempel et al. *J. Antibiotics* 22, Chemotherapy 1, 594–6 (1951)]. Other polyether antibiotics for which a coccidiostatic activity has been alleged include salinomycin and narasin.

Many of the polyether antibiotics have generally heretofore been recovered and employed in the form of their sodium salts. For example, a process for recovering lasalocid from its fermentation broth is disclosed in the Berger et al. article cited hereinbefore. In this process, the antibiotic or its alkali metal salts are extracted into various organic solvents in a multi-step operation.

As a more specific example, a process for the recovery of the polyether antibiotic carriomycin from fermentation beer was reported by Imada et al. *J. Antibiotics* 31, 7–14 (1978). In the disclosed process, fermented beer containing the carriomycin antibiotic was adjusted in pH with concentrated NaOH and acetone was then added. After stirring the mixture for 1 hour at room temperature, mycelia were filtered off and extracted again with acetone. The extracts were combined and concentrated in a vacuum until no acetone remained. The concentrated aqueous solution was extracted twice with equal volumes of ethyl acetate, followed by drying with anhydrous $Na_2SO_4$. The extracts were concentrated in a vacuum and passed through a column of activated charcoal, then the column was washed with ethyl acetate. The fractions active against *Staphylococcus aureus* FDA 209P were combined and the solvent was evaporated. To the oily residue was added n-hexane. The resultant solid material was collected by filtration and crystallized from aqueous acetone. On recrystallization from aqueous acetone, crystals of the mixed sodium and potassium salts of carriomycin were obtained, the mixture was dissolved in aqueous acetone and the solution was extracted twice with equal volumes of ethyl acetate. The extracts were dried with anhydrous $Na_2SO_4$ and concentrated to dryness in a vacuum. The resultant crystalline powder was recrystallized from aqueous acetone to yield carriomycin free acid.

As is apparent from the above recitation of one example of a known recovery process for a glycolic monovalent monoglycoside polyether antibiotic, such processes can be quite complicated and can require the use of relatively large quantities of various organic solvents, at least some of which may be quite expensive. In addition, such solvent recovery processes inevitably will suffer antibiotic yield losses as well as losses of the various organic solvents used in the process. There is thus a continuing need for antibiotic preparation and recovery processes which effectively and efficiently produce polyether antibiotics in a form suitable for use as feed additives.

In one aspect, the present invention relates to methods for producing zinc complexes of glycolic monovalent monoglycoside polyether antibiotics. In another aspect, the present invention relates to processes for the administration of zinc complexes of glycolic monovalent monoglycoside polyether antibiotics to poultry to promote poultry growth, to enhance poultry feeding efficiency, and/or to combat coccidial infections in poultry. In yet a further aspect, the present invention relates to feed compositions and feed additive compositions containing zinc complexes of linear monovalent polyether antibiotics and non-nitrogen containing divalent polyether antibiotics. In yet another aspect, the present invention relates to processes for stimulating cardiovascular function in animals by administering zinc complexes of polyether antibiotics. In a further aspect, the present invention relates to pharmaceutical compositions including zinc complexes of polyether antibiotics adapted for use in improving cardiovascular function in animals, particularly in mammals. In still another aspect, the present invention relates to methods for the purification of the zinc complexes of a polyether antibiotics which are formed in fermentation beers so that the zinc complexes are suitable for administration to a patient requiring improvement in cardiovascular function, e.g., myocardial stimulation. In all compositions and uses as are set forth above, the present invention is especially directed to zinc complexes of linear monovalent polyether antibiotics and non-nitrogen containing divalent polyether antibiotics.

For convenience, the terms "zinc complex" or "complex" are used hereinafter as meaning "a zinc complex of a polyether antibiotic."

In accordance with the present invention, zinc complexes of polyether antibiotics can be advantageously formed by adding water-soluble zinc salts to the fermentation broth in which such antibiotics have been produced. When formed in a fermentation beer, the formation of these complexes facilitates the recovery of the polyether antibiotics from the fermentation beer in which the antibiotics can be produced by, among other things, avoiding the necessity of using recovery methods which involve extractions with organic solvents followed by their subsequent purification and reuse. The resulting broth-insoluble zinc complexes of the antibiotics can then be recovered from the broth and employed, for instance, as coccidiostatic, feeding efficiency improving and growth-promoting agents for poultry. Upon further purification of the recovered zinc complexes by suitable methods the zinc complexes may be utilized in stimulating cardiovascular function in animals.

An antibiotic-containing fermentation broth can be prepared in conventional manner by fermenting a nutrient-containing liquid fermentation medium inoculated with a Streptomyces microorganism capable of producing the desired antibiotic. Suitable liquid fermentation media are generally aqueous dispersions containing a source of assimilable nitrogen and carbohydrates. Nitrogen sources for use in the fermentation media herein can include, for example, yeast, yeast-derived products, corn meal, bean meal, e.g., soy bean meal, etc. Carbohydrate sources for use in the fermentation media herein can include, for example, sugar, molasses, corn-steep liquor and the like. The fermentation media can also contain a variety of optional ingredients, if desired, such as for example, pH adjustment agents, buffers, trace minerals, antifoam agents, filter aids, etc.

The antibiotic can be prepared by growing the Streptomyces microorganism is an aerated, agitated, submerged culture with the pH of the broth adjusted to about neutral, i.e., from about 6.5 to 7.5. Fermentation can generally be carried out at slightly elevated temperatures, e.g., between about 25° C. and 35° C. Incubation of the broth can be carried out for a period of several days, e.g., from about 4 to 6 days or longer if it is economically advantageous to do so.

As was mentioned previously, polyether antibiotics for forming novel zinc complexes in accordance with the present invention include linear monovalent polyether antibiotics and non-nitrogen containing divalent polyether antibiotics, i.e., those polyether antibiotics which fall within classes 1a and 2a as defined by Westley, and which include monensin, nigericin, salinomycin, SY-1, narasin, laidlomycin, noboritomycin A & B, grisorixin, X-206, mutalomycin, alborixin and lonomycin; and lasalocid and lysocellin; respectively.

Monensin can be produced by inoculating the fermentation medium with a *Streptomyces cinnamonensis* microorganism. Such a microorganism is on unrestricted deposit under the number ATCC 15413 at the American Type Culture Collection, 12301 Parklawn Drive, Rockville, Md. 20852 (hereinafter referred to as the American Type Culture Collection).

Monensin is characterized chemically as 2-[5-ethyltetrahydro-5-[tetrahydro-3-methyl-5-[tetrahydro-6- hydroxy-6-(hydroxymethyl)-3,5-dimethyl-2H-pyran-2-yl]-2-furyl]-2-furyl]-9-hydroxy-α-methoxy- β,γ,2,8-tetramethyl-1,6-dioxaspiro[4.5]decane-7-butyric acid. This material has the following structural formula:

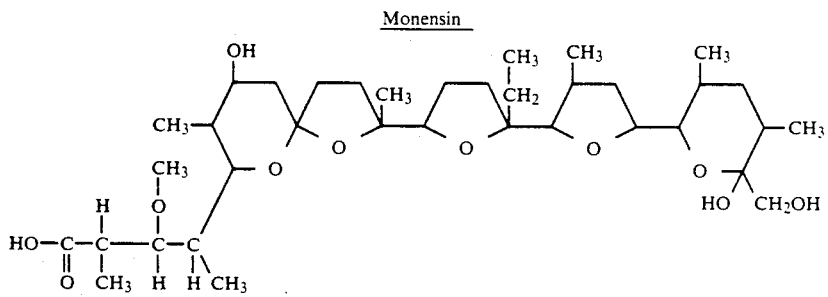

Monensin is described in greater detail in U.S. Pat. No. 3,501,568 and U.S. Pat. No. 3,794,732.

Nigericin can be produced by inoculating the fermentation medium with a *Streptomyces violaceoniger* microorganism. Such a microorganism is on unrestricted deposit at NRRL B1356 at the Northern Research and Development Division, Agricultural Research Service, United States Department of Agriculture, Peoria, Ill. (hereinafter referred to as the Agricultural Research Service).

Nigericin is characterized chemically as a stereoisomer of tetrahydro-6-([9-methoxy-2,4,10-trimethyl-2-[-tetrahydro-5-methyl-5-[tetrahydro-3-methyl-5-[tetrahydro-6-hydroxy-6-(hydroxymethyl)-3,5-dimethyl-2H-pyran-2-yl]-2-furanyl]-2-furanyl]-1,6-dioxaspiro(4.5) dec-7-yl]-methyl]-α,3-dimethyl-2H-pyran-2-acetic acid). This material has the following structural formula:

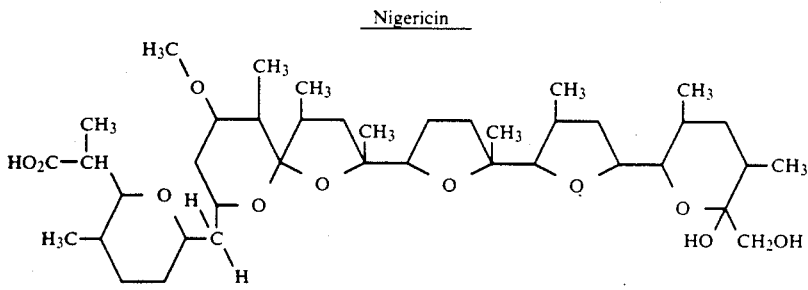

Nigericin is also known by the names polyetherin A, antibiotic X-464, antibiotic K178, helexin C and azolomycin M. Nigericin (and its characteristics and preparation) is described in greater detail in U.S. Pat. No. 3,555,150; U.S. Pat. No. 3,794,732. Harned et al. *Antibiotics and Chemotherapy*, Vol. 1, No. 9 (December, 1951) pp. 594-596; Steinrauf et al., *Biochemical and Biophysical Research Communications*, Vol. 33, No. 1 (1968) pp. 29-31 and Stempel et al., *The Journal of Antibiotics*, Vol. XXII, No. 8 (August, 1969) pp. 384-385.

The salinomycin antibiotic can be produced by innoculating a fermentation medium with a *Streptomyces albus* microorganism which is on deposit under number ATCC 21838 at the American Type Culture Collection mentioned previously. Salinomycin was reported by Miyazaki et al., *J. Antibiotics* 27, 814-21 (1974) as having the following structural formula:

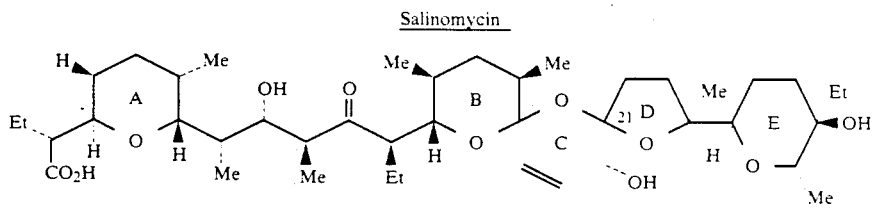

This article sets forth methods of preparation and properties of salinomycin and U.S. Pat. No. 3,857,948 to Tanaka et al. also discloses methods for the preparation of the salinomycin antibiotic.

The antibiotic narasin (also known as 4-methylsalinomycin) can be produced by innoculating a fermentation medium with a *Streptomyces aureofaciens* microorganism which is on unrestricted deposit at the Agricultural Research Service mentioned previously under culture numbers NRRL 5758 and 8092. The structure of narasin was reported by Berg et al., *J. Antibiotics* 31, 1-6 (1978) as the following:

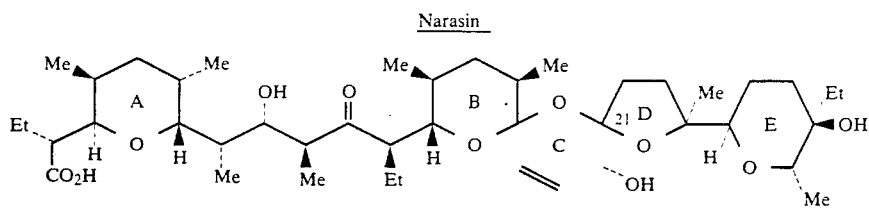

Narasin

The antibiotic is also the subject of U.S. Pat. Nos. 4,035,481 and 4,038,384 to Berg et al.

The antibiotics noboritomycin A and B are the fermentation products of the microorganism *Streptomyces norboritoensis* which is on deposit at Agricultural Research Service under the number NRRL 8123. A method for the preparation of these antibiotics and their chemical structure was reported by Keller-Juslén et al. in *J. Antibiotics* 31, 820-828 (1978). The antibiotics have the structural formula:

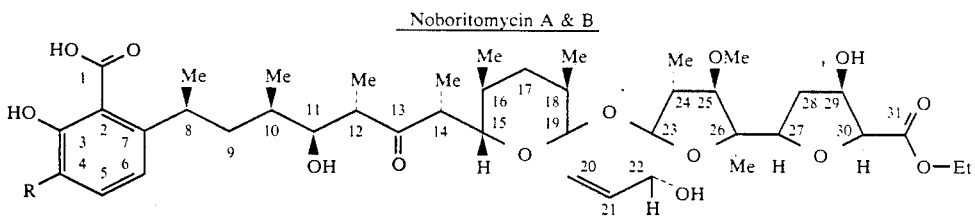

Noboritomycin A & B

In noboritomycin A, R is methyl and in norboritomycin B, R is ethyl.

The antibiotic grisorixin is produced from the microorganism *Streptomyces griseus* as reported by Gachon et al., *Chem. Comm.*, 1421-1423 (1970) and *J. Antibiotics* 28, 345-350 (1975). As is disclosed in U.S. Pat. No. 4,161,520 to Osborne et al., the microorganism is on deposit at the Institut National de la Recherche Agronomique where it has been assigned the designation INRA SAB 2142. Grisorixin is structurally very similar to nigericin, the only difference being the presence of an additional oxygen in nigericin. The structural formula for grisorixin is:

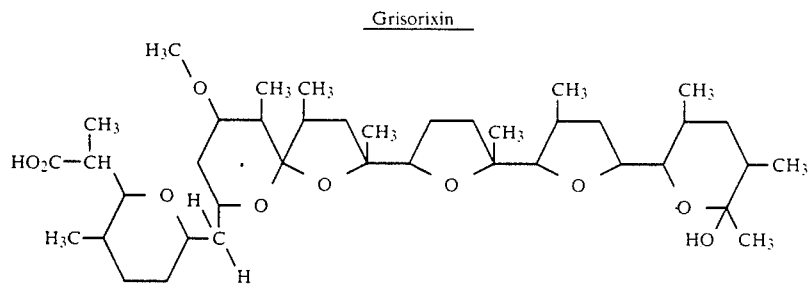

Grisorixin

Various derivatives of grisorixin are disclosed by Gachon et al., *J. Antibiotics* 28, 351-357 (1975).

Antibiotic X-206 was first reported by Berger et al., *J. Am. Chem. Soc.* 73, 5295-5298 (1951) and has the following structure as reported by Blount et al., *Chemical Communications*, 927-928 (1971):

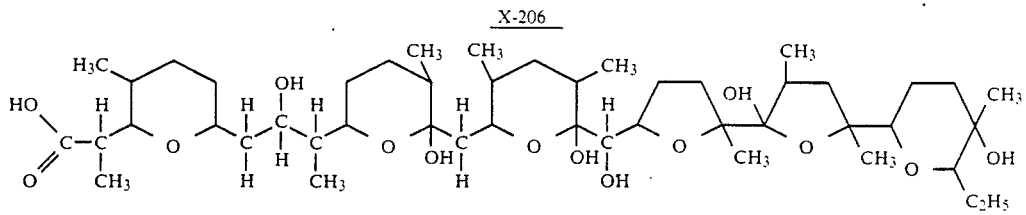

X-206

Methods for preparation of the X-206 antibiotic as well as further particulars as to its properties are set forth in U.S. Pat. Nos. 3,839,557 to Raun and 3,794,732 to Raun.

The antibiotic lonomycin has the following structural formula as reported by Mitani et al., *J. Antibiotics* 31, 750-755 (1978):

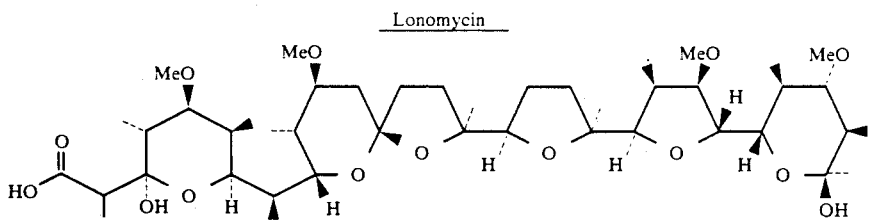

Lonomycin

A method for producing the antibiotic is set forth by Omura et al., *J. Antibiotics* 29, 15-20 (1976). The antibiotic was also identified by Oshima et al., *J. Antibiotics* 29, 354-365 (1976) as DE-3936 and was determined to be identical to emercid reported by Riche et al., *J.C.S. Chem. Comm.* 1975, 951-952 (1975) and to 31,559RP reported by Rhone Poulenc: Japan Patent, Kokai 50-129, 796 (Oct. 14, 1975). U.S. Pat. No. 3,950,514 to Sawada et al. discloses the lonomycin antibiotic as being produced by the *Streptomyces ribosidicus* microorganism which has been deposited under number ATCC 31051 at the American Type Culture Collection.

The following structural formula was set forth by Gachon et al., *J. Antibiotics* 29, 603-610 (1976) for the antibiotic alborixin:

cherche Agronomique and assigned the designation INRA SAB 3840.

Mutalomycin is produced by strain S11743/A of the *Streptomyces mutabilis* microorganism which has been deposited at the Agricultural Research Service under number NRRL 8088. A method for preparing the antibiotic and its physical and chemical properties were reported by Fehr et al. *J. Antibiotics* 30, 903-907 (1977). The structural formula of mutalomycin is:

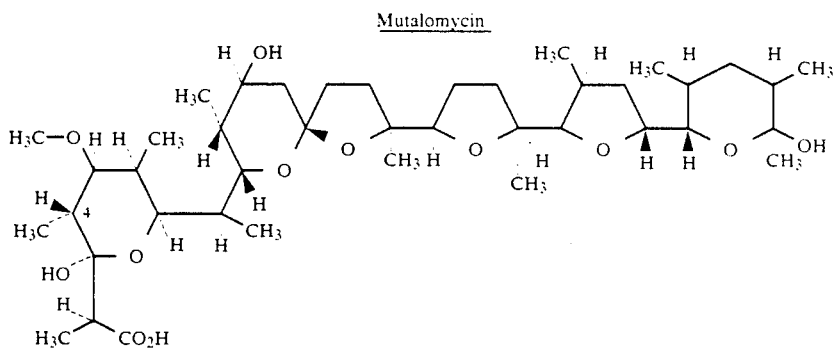

Mutalomycin as reported by Fehr et al. *J. Antibiotics* 32, 535-536 (1979).

The antibiotic laidlomycin has been described by Kitame et al., *J. Antibiotics* 27, 884-887 (1974), the antibiotic being produced by the *Streptomyces eurocidicus* var. asterocidicus microorganism which has been in-

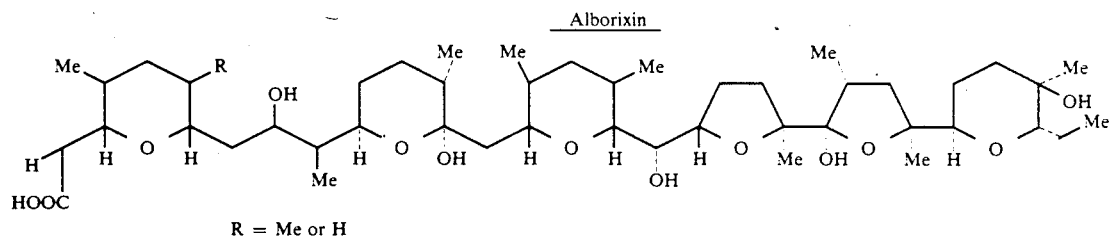

Alborixin

R = Me or H

Certain characteristics of the antibiotic were set forth in the article by Delhomme et al., *J. Antibiotics* 29, 692-695 (1976). The alborixin antibiotic is produced from a *Streptomyces albus* microorganism and as is disclosed in U.S. Pat. No. 4,161,520 to Osborne et al., the microorganism is on deposit at the Institut National de la Recherche dexed as species S-822 at the Department of Bacteriology, Tohoku University School of Medicine, Sendai, Japan. The chemical structure of laidlomycin was reported by Westley, *Adv. Appl. Microbiology* 22, 177-223 (1977) as being:

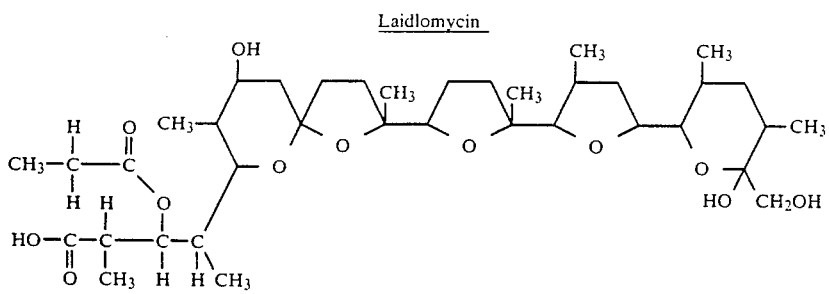

Laidlomycin

The laidlomycin antibiotic also appears to be the subject of U.S. Pat. No. 1,016,256 to Ishida et al.

The antibiotic SY-1 is the fermentation product of a *Streptomyces albus* microorganism, a culture of which has been deposited at the American Type Culture Collection under accession number ATCC 21838. As is set forth in U.S. Pat. No. 4,138,496 to Shibata et al., the SY-1 antibiotic has the following structural formula:

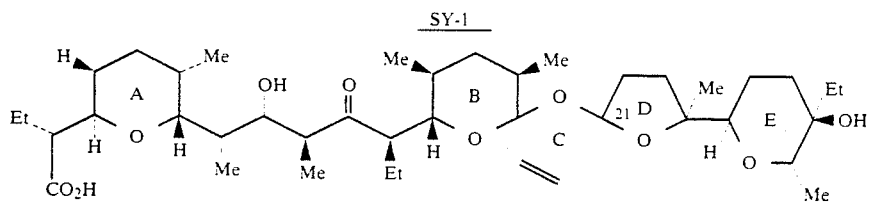

SY-1

The structure of the SY-1 antibiotic is quite similar to that of salinomycin, the only apparent structural difference being that salinomycin contains a hydroxyl group on the ring designated "C".

Lasalocid can be prepared by inoculating the fermentation medium with a *Streptomyces lasaliensis* microorganism. Lyophilized tubes of this culture bearing the laboratory designation X-537A were deposited with the United States Department of Agriculture, Agricultural Research Service, North Utilization Research and Development Division, Peoria, Ill. The culture, given identification number NRRL 3382 by the Agricultural Research Service, has been made available to the public through NRRL. The culture is also available to the public from the International Center of Information in collaboration with the World Health Organization in Belgium.

The lasalocid antibiotic produced has been chemically identified in U.S. Pat. No. 4,164,586 to Westley as 6-[7(R)-[5(S)-ethyl-5(5(R)-ethyltetrahydro-5-hydroxy-6(S)-methyl-2H-pyran-2(R)-yl)tetrahydro-3(S)-methyl-2(S)-furyl]-4(S)-hydroxy-3(R),5-(S)-dimethyl-6-oxononyl]-2,3-cresotic acid. This antibiotic has the following structural formula:

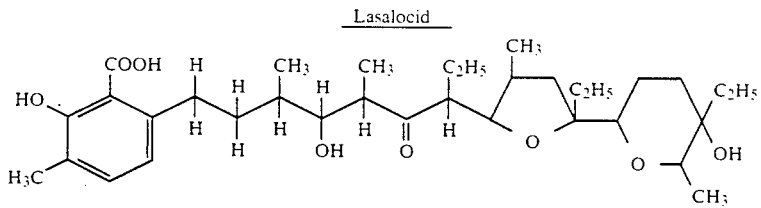

Lasalocid

A method for producing the antibiotic lysocellin was disclosed by Liu et al. in U.S. Pat. No. 4,033,823 by the cultivation of a strain of *Streptomyces longwoodensis* which is on deposit at the American Type Culture Collection under the designation ATCC 29251. The structure of lysocellin is as follows:

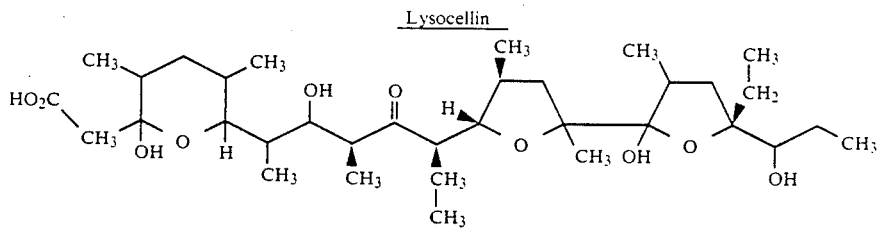

Lysocellin

Suitable methods for preparing the lysocellin antibiotic are set forth in the above-mentioned patent. The characteristics of lysocellin were first set forth in the article by Ebata et al., *J. Antibiotics* 28, 118–121 (1975).

While the above descriptions of the various known polyether antibiotics have generally identified the antibiotics as being single compounds, it should be recognized that at least some of the polyether antibiotics are produced as an antibiotic complex of structurally related factors containing varying proportions of each factor. As an example, the structure for lasalocid set forth previously is lasalocid factor A which is produced in combination with factors B-E in ratios depending upon fermentation conditions. Homologs of lasalocid A are disclosed in U.S. Pat. No. 4,168,272 to Westley. An isomeric form of lasalocid is also known from U.S. Pat. No. 3,944,573 to Westley. In addition, monensin is produced With factors B and C as reported by Westley, *Adv. Appl. Microbiology* 22, 200 (1977) and narasin is produced with factors A, B and D as is set forth in U.S. Pat. No. 4,038,384 to Berg et al. It should therefore be realized that the present invention comprehends the zinc complexes of the various factors of the polyether antibiotics whether in combination with other factors or in their isolated form as well as their use in promoting growth, enhancing feeding efficiency and treating coccidial infections in poultry, and in stimulating cardiovascular function in animals.

Furthermore, zinc complexes of derivatives of the previously mentioned polyether antibiotics are also within the scope of the present invention. For example, various derivatives of the lasalocid antibiotic are known from U.S. Pat. No. 3,715,372 to Stempel et al. In addition, derivatives of monensin are disclosed in U.S. Pat. No. 3,932,619 to Brannon et al. which is directed to a metabolite produced from monensin, U.S. Pat. No. 3,832,258 to Chamberlain which is directed to the deshydroxymethyl derivative of monensin and U.S. Pat. Nos. 4,141,907 and 4,174,404 to Nakatsukasa et al. are directed to deoxynarasin. Therefore, as used herein, the specific name of the polyether antibiotic, e.g. lasalocid, encompasses all of the factors of the antibiotic, e.g. lasalocid A-E, as well as isomers thereof, e.g. iso-lasalocid, and derivatives thereof.

For further particulars as to characteristics and methods for the preparation of certain of the above polyether antibiotics, reference is made to U.S. Pat. No. 3,995,027 to Gale et al. and the patents cited therein and to U.S. Pat. No. 3,794,732 to Raun and the patents and articles cited therein.

It is also within the scope of the present invention that the zinc complexes of linear monovalent and nonnitrogen containing divalent polyether antibiotics can be used in conjunction with other active ingredients which are also useful for challenging coccidial infections in poultry and/or for promoting growth and enhancing feed efficiency in poultry. For example, the zinc complexes of polyether antibiotics may have an enhanced effect when used in combination with metichlorpindol. The use of metichlorpindol with monensin for treatment of poultry coccidiosis is described in U.S. Pat. No. 4,061,755 to McDougald. Compositions containing certain designated polyether antibiotics and a pleuromutilin derivative which are useful in treating poultry coccidiosis are disclosed in U.S. Pat. No. 4,148,890 to Czok et al.

To the extent necessary, the above-mentioned patents and literature articles mentioned in describing the various known polyether antibiotics are incorporated herein by reference.

In accordance with the present invention, the polyether antibiotic, generally in the form of its alkali metal, alkaline earth metal or ammonium salt, is treated in situ in the fermentation broth or beer by adding to the antibiotic containing broth a water-soluble zinc salt. Addition of such a water-soluble zinc salt promotes the formation of a zinc complex of the polyether antibiotic. Such a zinc complex of the antibiotic, along with zinc complexes formed with residual nitrogen-containing compounds in the broth such as amino acids, polypeptides, and proteins, are insoluble in the fermentation broth liquid.

The zinc ions from the added zinc salt apparently form coordination bonds with the oxygen atoms of the insoluble zinc antibiotic complex. For example, the structure of the zinc complex of lasalocid is believed to be represented by the following:

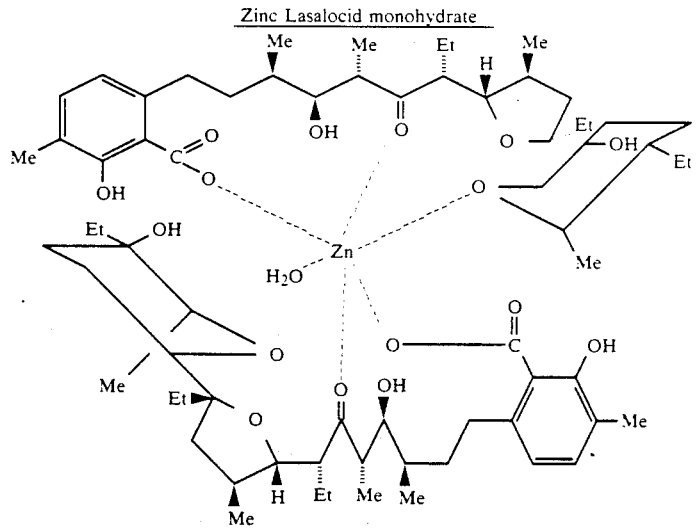

Zinc Lasalocid monohydrate

On the basis of the formation constants with ligands such as citric acid, lactic acid, and tartaric acid, zinc ions form stronger bonds with oxygen-containing compounds than do ions such as $Mg^{++}$, $Ca^{++}$, $Ba^{--}$, $Na^+$, and $K^+$.

The zinc salt added to the fermentation broth can be various water-soluble salts which ionize in the fermentation broth. Such salts include, for example, zinc chloride, zinc sulfate, zinc acetate, zinc benzoate, zinc citrate, zinc lactate, etc. Water-soluble zinc salts are generally those which can be dissolved to the extent of about 1 percent by weight or more in water at 20° C. For maximum production of the desired zinc complexes, water-soluble zinc salt should be added to the fermented broth in an amount which is sufficient to fill substantially all of the possible zinc coordination sites of the proteins, polypeptides, amino acids and related compounds, in addition to substantially all of the available coordination sites of the antibiotic present. This is necessary because in general, nitrogen atoms in the polypeptides, amino acids, etc., form stronger coordination bonds with zinc than do the oxygen atoms in the polyether antibiotic. Generally, therefore, zinc salt is added to the fermentation broth in an amount sufficient to provide a zinc content of from about 3 to 12 percent and preferably from about 5 to 10 percent by weight of the dried precipitate recovered from the fermentation broth as hereinafter more fully described.

The amount of soluble zinc salt to be added will depend on the amount of nutrients added to the fermentation broth during the course of the fermentation. An actual amount of soluble zinc salt to be added to broth obtained from a given mash bill can be determined by simple laboratory precipitations followed by zinc analyses on the dried precipitates. When, for example, the preferred zinc chloride salt is employed to form the desired zinc antibiotic complex, advantageously from about 4 to 10 gallons of a 67 weight percent zinc chloride solution (sp. gr. 1.883), can be added to 1000 gallons of fermentation broth.

To form the zinc antibiotic complex in the fermentation broth, pH of the broth is advantageously adjusted to about 6.5 to 7.5 and preferably to about 6.8 to 7.2 after addition of the soluble zinc salt to the fermentation broth.

The insoluble zinc complexes formed upon addition of zinc salt can be readily separated from the fermentation broth or beer by conventional filtration or centrifugation techniques. In this manner, a wet biomass, containing the zinc antibiotic complex, is realized. This wet biomass is resistant to wild fermentations because of its relatively high zinc content. The wet biomass so obtained is easily dried by spray drying or drum drying procedures, and this zinc antibiotic-containing dried product can then be used as a feed additive per se. If the antibiotic content of the fermentation beer is lower than desired after completion of the fermentation, crude antibiotic in its sodium salt form can be added to the fermentation beer prior to the addition of the soluble zinc salt. In this manner, the antibiotic content of the biomass composition to be separated from the broth can be increased. To be suitable as a feed additive, the dried biomass preferably contains at least about 5 percent by weight of the zinc antibiotic complex, advantageously from about 10 percent to 50 percent by weight of the zinc antibiotic complex.

Recovery of the zinc antibiotic complexes of the present invention in the manner described herein provides several important advantages over known antibiotic preparation and recovery processes. The present process, for example, provides a means for recovering relatively high yields of antibiotic in a salable feed additive product. Further, the use of expensive extraction solvents and the cost associated with the process losses of such solvents are avoided. The present process also permits recovery of salable feed values present in the mycelium of the Streptomyces microorganism used to produce the antibiotic. The present process further reduces the cost of waste disposal operations needed in previous processes to deal with the mycelial mat produced during fermentation. Use of this mat as part of the feed additive product, in fact, reduces the cost of the carrier for the antibiotic material being marketed.

The dried, antibiotic-containing biomass recovered from the fermentation broth as hereinbefore described can be added to conventional poultry feed compositions as a coccidiostatic and growth-promoting agent. Such feed compositions generally contain whole or ground cereal or cereal byproducts as an essential nutrient. The feed compositions can also contain such optional additional materials as animal byproducts, e.g., bone meal, fish meal, etc., carbohydrates, vitamins, minerals, and the like. The zinc antibiotic complexes of the present invention are generally employed in the feed compositions to the extent of from about 50 grams per ton to 200 grams per ton, preferably from about 75 grams per ton to 125 grams per ton.

As was mentioned previously, the zinc complexes of polyether antibiotics according to the present invention may also be utilized for the stimulation of cardiovascular functions and particularly in the treatment of ailments such as cardiogenic shock, septic shock and congestive heart failure. Preferably, the zinc complexes are utilized for these purposes in a purified form and are administered either orally or parenterally to a patient requiring treatment. Oral administration is particularly preferred for long term treatment of chronic diseases such as congestive heart failure while parenteral administration is preferred for emergency treatment such as in the treatment of shock and of acute heart failure.

Purification of the zinc complexes of the present invention so that the complexes are more suitable for administration to humans can be accomplished in a variety of manners. A presently preferred method for purification of the zinc complexes from the recovered feed grade zinc complex includes the steps of, after treatment of the fermentation beer with a soluble zinc salt, acidifying the water slurry of the zinc complex with strong mineral acid such as sulfuric acid to produce a relatively low pH, e.g. a pH below about 4, preferably about 2 to about 3, and then extracting the acid form of the polyether antibiotic from the slurry into a substantially water-insoluble organic solvent such as butyl acetate.

Thereafter, a lower aliphatic alcohol such as methanol is added to the organic solvent containing the polyether antibiotic. The volume of alcohol added is generally less than or about equal to the volume of organic solvent, preferably about 0.25 to about 1.0 volumes alcohol to about 1.0 volume of organic solvent. A soluble zinc salt such as zinc chloride in the same lower aliphatic alcohol is then slowly added with vigorous agitation to the organic solvent-alcohol mixture containing the polyether antibiotic so as to form the zinc complex of the polyether antibiotic. Preferably, about 0.5 to 1.0 volumes of the alcohol containing the zinc salt are added per volume of mixture The amount of zinc salt added should be sufficient to convert essentially all of the contained antibiotic to its zinc complexed form. The formed zinc complexes are then filtered from the mixture, thoroughly washed, and dried.

If greater purification of the zinc complex is desired, the above procedure can be modified to include further purification steps. One such modification is, prior to the addition of the lower aliphatic alcohol, adding an aqueous solution containing an alkali metal hydroxide such as potassium or sodium hydroxide to the organic solvent containing the polyether antibiotic so that the antibiotic is extracted into the aqueous solution. The antibiotic is then re-extracted into the same organic solvent or a different water-insoluble organic solvent such as methyl tertiary-butyl ether after acidification. These steps of the modified procedure can be repeated as many times as desired until the proper degree of purification is achieved. Thereafter, the polyether antibiotic is contacted with the lower aliphatic alcohol and the previously mentioned procedure continued so as to yield the purified zinc complex of the polyether antibiotic.

In the above description of the purification procedure and modification thereof, the amount of each of the media, i.e., the organic solvent, aliphatic alcohol, aqueous solution, etc., relative to the others when conducting the procedure may vary considerably, the primary considerations being that sufficient media be utilized to obtain a satisfactory yield of the zinc complex balanced against the cost of the media and the capacity of the available equipment. Generally, the amount of a particular medium used to treat another medium in any of the steps of the above procedure is about 0.1 to 10 volumes, preferably about 0.5 to about 5 volumes, for each volume treated.

Certain advantages are realized by the above procedure where the purified zinc complexes are recovered from the feed grade complexes as opposed to recovery of the purified complexes from virgin mycelia. Among others, the feed grade complexes are filtered relatively easily from the fermentation beer whereas filtering of virgin mycelia is very slow and thus time-consuming. In addition, the feed grade complexes tend to be more concentrated and thus less organic solvent is required in conducting the purification procedure and volume loss of solvent will be reduced.

The zinc complexes of the present invention may be formulated with conventional inert pharmaceutical carrier or adjuvant materials into dosage forms which are suitable for oral or parenteral administration to stimulate cardiovascular function. Such dosage forms include tablets, suspensions, solutions, hard or soft capsules, dragees and the like. The selection of suitable materials which may be used in formulating the active zinc complexes into oral and parenteral dosage forms will be apparent to persons skilled in the art. Such materials, either inorganic or organic in nature, should be of pharmaceutically acceptable quality, free from deleterious impurities and may include, for example, water, dimethylsulfoxide, gelatin albumin, lactose, starch, magnesium stearate, preservatives, stabilizers, wetting agents, emulsifying agents, salts for altering osmotic pressure, buffers, etc. which can be incorporated, if desired, into such formulations.

The quantity of zinc complex which may be present in any of the above described dosage forms generally varies from 10 to 100 mg. per unit dosage. The dosage administered to a particular patient is variable, depending upon the clinician's judgment using the criteria of the condition and size of the patient, the potency of the zinc complex and the patient's particular response thereto. An effective dosage amount of the zinc complex can therefore only be determined by the clinician utilizing his best judgment on the patient's behalf. Generally, parenteral doses should be from about 20 mg. to about 50 mg. for the average size person. Smaller persons or larger persons may require adjustments due to body size. Oral doses, usually capsules, but tablets can be used, generally contain about twice the parenteral dose. The frequency of the administration of the zinc complex depends generally upon the patient's condition and the desired response from the patient. Chronically ill patients may require administration every 2 to 3 hours or once a day, depending on the severity of the disease and the patient's particular response to treatment. Emergency patients generally require only one dose of the zinc complex, particularly those patients in shock.

When administered to a patient requiring treatment, the zinc complexes of the present invention generally have a positive inotropic effect with little or no chronotropic effects and display minimal, if any, adrenergic action, have a rapid onset of action, require a small effective dose, are non-toxic at the effective doses, have a satisfactory duration of action, display a return to the original pre-drug values of cardiovascular activity, and exhibit continued generally identical responses to subsequently repeated identical dosages.

Illustrated in the following examples are preparation and recovery methods for the zinc complexes of polyether antibiotics as well as feed and feed additive compositions including these zinc complexes and their usefulness as coccidiostats and growth-promoting agents for poultry and in addition, pharmaceutical compositions including these zinc complexes and their usefulness in stimulating cardiovascular function. These examples are in no way to be considered limiting of the present invention to compositions, ingredients, and processes involving that particular material.

EXAMPLE I

A. Fermentation

About 450 ml of inoculum of *Streptomyces lasaliensis* culture No. NRRL 3382R, obtained from the Northern Utilization Laboratory, Peoria, Ill., is introduced into 9,000 ml of fermentation medium of the following composition:

| | |
|---|---|
| Soybean Flour | 2% |
| Brown Sugar | 2% |
| Corn Steep Liquor | 0.5% |
| $K_2HPO_4$ | 0.1% |
| Hodag Antifoam K-67 | 0.05% |
| Water | Balance |
| | 100.00% |

The fermentation is conducted in a 20-liter, stainless steel fermentor using the conditions listed below.
1. Amount of medium—9.45 liters.
2. Temperature—28° C.
3. Air Flow—9.0 liters per minute.
4. Mechanical agitation—One 13-cm. diameter impeller rotating at 600 RPM.
5. Back pressure—about 16.7 psig.
6. Time of fermentation—72 hours.

At the end of the fermentation the lasalocid assay of the beer is 1.5 g per liter.

B. Recovery

Since the assay of the beer for lasalocid is low compared to assays commonly obtained for antibiotics, the beer is spiked with crude lasalocid which has been obtained by extracting with butyl acetate commercial product containing approximately 81 grams of sodium lasalocid per pound.

Twenty-five grams of crude sodium lasalocid (78.5% lasalocid) dissolved in 150 ml of methanol are added to 2000 ml of beer under constant agitation. After thorough agitation, 12.5 ml of a zinc chloride solution (0.24 g Zn per ml) are slowly added with agitation to the fermented beer. The pH is adjusted to a value in the range 7.0-7.4.

After the treated beer has been agitated for about 30 minutes it is filtered, without filter aid, on a Buckner funnel using No. 1 Whatman filter paper. The filtration proceeds rapidly to give a firm cake which is dried in an oven. The final dried product weighs 57 grams and has an assay of 32.7% lasalocid.

The calculated recovery from beer to dried product is 82.4% derived from the following formula.

$$\frac{0.327 \times 57}{2 \times 1.5 + 25 \times 0.785} \times 100\% = 82.4\%$$

EXAMPLE II

Objective

To determine the efficacy of the new zinc lasalocid complex as an anticoccidial compound for poultry, zinc lasalocid is tested in comparison with Coban (monensin sodium) in chickens which are challenged by *Eimeria tenella*.

| Test Animals: | Species: Avian | Total Number: | 24 birds/ treatment |
|---|---|---|---|
| Initial Age: 14 days | Breed: Hubbard White Mountain | Sex: Male | Initial Weight: 330 g |

Test Materials

Zinc lasalocid - 32.7% pure by weight
Coban (monensin sodium) - Lot No. X31211

Test Procedure

1. At 14 days of age chicks are weighed and assigned to groups. Immediately after groups are formed (composed of 12 chicks each) chicks are started on their respective medicated feed ration. Each treatment group is replicated twice for a total of 24 birds per group.

2. Seventy-two hours after the initiation of medication, birds are orally inoculated with approximately 100,000 *Eimeria tenela* oocysts suspended in a 1 cc dose.

3. Controls consist of an infected non-medicated group, a non-infected group and an infected group treated with Coban.

4. Criteria for evaluation are a. Morbidity (4th-6th day)
b. Mortality (4th-7th day)
c. Incidence of bloody droppings (4th-6th day)
d. Body weight gain
e. Feed per gain
f. Postmortem lesions.

Treatment Groups

| Pen | Treatment |
|---|---|
| 4, 9 | Zinc lasalocid, 75 g/ton |
| 1, 6 | Zinc lasalocid, 113 g/ton |
| 5, 12 | Zinc lasalocid, 150 g/ton |
| 7, 11 | Coban, 110 g/ton |
| 3, 8 | Non-inoculated control |
| 2, 10 | Inoculated control |

Rations

Rations employed in the Example II testing are summarized in Table 1.

TABLE 1

| Chick Starter (Corn) | | | |
|---|---|---|---|
| % Protein | 23.0 | % Calcium | .98 |
| M.E. Kilocalories/lb | 1376* | % Total phosphorus | .89 |

| | |
|---|---|
| Ground yellow corn | 55.0 |
| Soybean meal 44% | 29.0 |
| Fish solubles | 2.0 |
| Meat and bone | 5.0 |
| Dehydrated alfalfa meal | 1.2 |
| Dried whey | 1.0 |
| Animal tallow | 4.0 |
| Dicalcium phosphate | 1.0 |
| Hubbard super-13 | 0.8 |
| Vitamin and trace mineral premix | 0.5 |
| Salt | 0.5 |
| | 100.5 |

*M.E. - Metabolizable Energy

Test Results

Results of the Example II testing are summarized in Table 2.

TABLE 2

| Treatment | Pen No. | Mortality | Morbidity | Incidence of[1] Bloody Droppings | Body Weight Gain, g | Feed/ Gain | Postmortem Lesions |
|---|---|---|---|---|---|---|---|
| Non-inoculated Control | 3 | 0/12 | 0/12 | None | 208.42 | 1.56 | None |
| | 8 | 0/12 | 0/12 | None | 220.00 | 1.54 | None |
| | | 0/24 | 0/24 | None | 214.21 | 1.55 | None |
| Inoculated Control | 2 | 2/12 | 9/12 | Severe | 65.80 | 2.50 | Severe |
| | 10 | 2/12 | 10/12 | Severe | 47.80 | 2.79 | Severe |
| | | 4/24 | 19/24 | Severe | 56.80 | 2.65 | Severe |
| Coban 100 g/T | 7 | 0/12 | 0/12 | Slight | 178.17 | 1.80 | None |
| | 11 | 0/12 | 2/12 | Slight | 166.92 | 1.75 | None |
| | | 0/24 | 2/24 | Slight | 172.55 | 1.78 | None |
| Zinc lasalocid 75 g/T | 4 | 0/12 | 0/12 | None | 226.92 | 1.52 | None |
| | 9 | 0/12 | 0/12 | None | 228.25 | 1.36 | None |
| | | 0/24 | 0/24 | None | 227.59 | 1.44 | None |

TABLE 2-continued

| Treatment | Pen No. | Mortality | Morbidity | Incidence of[1] Bloody Droppings | Body Weight Gain, g | Feed/ Gain | Postmortem Lesions |
|---|---|---|---|---|---|---|---|
| Zinc lasalocid 113 g/T | 1 | 0/12 | 0/12 | None | 232.00 | 1.50 | None |
| | 6 | 0/12 | 0/12 | None | 229.58 | 1.42 | None |
| | | 0/24 | 0/24 | None | 230.79 | 1.46 | None |
| Zinc lasalocid 150 g/T | 5 | 0/12 | 0/12 | None | 204.25 | 1.48 | None |
| | 12 | 0/12 | 0/12 | None | 218.92 | 1.59 | None |
| | | 0/24 | 0/24 | None | 211.59 | 1.54 | None |

[1] Bloody droppings:
None - 0
Slight - <10
Moderate - 10-30
Severe - >30

The results of Table 2 show that a satisfactory challenge is obtained with *E. tenella* and that all three levels of zinc lasalocid demonstrate excellent activity against this organism. In fact the birds receiving the two lower levels of zinc lasalocid also show superiority over the controls in weight gain and in feed efficiency. Furthermore, zinc lasalocid gives results superior to those obtained with Coban in controlling *E. tenella*, in weight gain and in feed efficiency.

EXAMPLE III

An experiment is run to confirm the indication in Example II that zinc lasalocid has growth promoting for chickens.

Objective

To determine the efficacy of zinc lasalocid for promoting the growth and improving feed efficiency in broiler chicks.

| Test Animals: | Species: Avian | Total Number: | 60 birds/ treatment |
|---|---|---|---|
| Initial Age: 2 days | Breed: Hubbard White Mountain | Sex: Male | Initial Weight: 43 g |
| Duration of Test: 13 days | | | |

Two-day old broiler type chicks are placed into Petersime starter batteries and given feed and water ad libitum for the duration of the test. Chicks are divided into four treatment groups which are replicated six times with ten chicks (males) in each replication. The test period is 13 days. Pen live body weights are taken at 2, 7 and 14 days of age. Pen feed efficiency measurements are taken at 14 days of age.

Rations

Rations employed in the testing are summarized in Table 3.

TABLE 3

| Chick Starter (Rye) | | | |
|---|---|---|---|
| % Protein | 23.2 | % Calcium | 0.98 |
| M.E. kilocalories/lb | 1260* | % Total phosphorus | 0.89 |
| Ground Rye | | | 55.0 |
| Soybean meal 44% | | | 29.0 |
| Fish solubles | | | 2.0 |
| Meat and bone meal | | | 5.0 |
| Dehydrated alfalfa meal | | | 1.2 |
| Dried Whey | | | 1.0 |
| Animal tallow | | | 4.0 |
| Dicalcium phosphate | | | 1.0 |
| Hubbard Super-13 mineral | | | 0.8 |
| Vitamin and trace mineral premix | | | 0.5 |
| Salt | | | 0.5 |
| | | | 100 lbs |

*M.E. - Metabolizable Energy

Test Results

Results of the Example III testing are summarized in Table 4.

TABLE 4

| | Mean Body Weight Gain and Feed/Gain Ratio (F/G) | | | | |
|---|---|---|---|---|---|
| Treatment | Pen No. | Body Weight Gain, g | % Increase | F/G | % Increase |
| Control | 242 | 154.30 | | 1.64 | |
| | 243 | 143.80 | | 1.70 | |
| | 252 | 156.80 | | 1.52 | |
| | 257 | 153.90 | | 1.62 | |
| | 260 | 156.80 | | 1.71 | |
| | 261 | 158.20 | | 1.67 | |
| Average | | 153.97 | — | 1.64 | — |
| Zinc Lasalocid 50 g/ton | 241 | 230.50 | | 1.35 | |
| | 246 | 246.40 | | 1.36 | |
| | 249 | 235.70 | | 1.43 | |
| | 256 | 215.89 | | 1.38 | |
| | 259 | 226.50 | | 1.35 | |
| | 264 | 236.30 | | 1.40 | |
| Average | | 231.88[a] | 50.6 | 1.38[a] | 15.2 |
| Zinc Lasalocid | 244 | 226.80 | | 1.38 | |

TABLE 4-continued

| | | Mean Body Weight Gain and Feed/Gain Ratio (F/G) | | | |
|---|---|---|---|---|---|
| Treatment | Pen No. | Body Weight Gain, g | % Increase | F/G | % Increase |
| 100 g/ton | 247 | 252.20 | | 1.35 | |
| | 250 | 254.40 | | 1.39 | |
| | 253 | 267.44 | | 1.30 | |
| | 258 | 245.80 | | 1.33 | |
| | 263 | 248.22 | | 1.35 | |
| Average | | 249.14[a] | 61.8 | 1.35[a] | 17.7 |

[a]Means are significantly different at the P <0.01 level of probability compared to controls.

The results of Example III show that, at levels of 50 and 100 grams per ton, zinc lasalocid greatly improves growth response and feed efficiency of young broiler chicks.

EXAMPLE IV

Objective

To compare efficacy of zinc lasalocid against lasalocid and zinc bacitracin for promoting growth and improving feed efficiency in the chick.

| Test Animals: | Species: Avian | Total Number: | 60 birds/ Treatment |
|---|---|---|---|
| Initial Age: 2 days | Breed: Hubbard White Mountain | Sex: Males | Initial Weight: 36 g |
| Duration: 14 days | | | |

Test Procedure

Two day old broiler type chicks are placed into Petersime starter batteries and given feed and water ad libitum for the duration of the test. Chicks are randomly divided into four treatment groups which are replicated six times with 10 chicks (males) in each replication. The test period was 14 days. Pen live body weights are taken at 2, 7 and 15 days of age. Pen feed efficiency measurements are taken at 15 days of age.

| | Treatment Groups: | |
|---|---|---|
| Pen | Treatment | Lot No. |
| 241, 246, 249 256, 259, 264 | Control | |
| 245, 248, 251 254, 255, 262 | Lasalocid[1], 50 g/ton | P-446 E |
| 244, 247, 250 253, 258, 263 | Zinc bacitracin[2], 50 g/ton | 11207902 |
| 242, 243, 252 257, 260, 261 | Zinc lasalocid[3], 50 g/ton | Prepared by Procedure of Example I |

[1]Lasalocid - 68 g/lb (Avatec)
[2]BACIFERM-10
[3]Zinc lasalocid - 32.7% lasalocid by wt.

Rations

The composition of the chick starter ration is given in Table 3 of Example III.

Test Results

Results of the Example IV testing on growth and feed efficiency are summarized in Table 5.

TABLE 5

| | | MEAN Body Weight Gain and Feed/Gain Ratio (F/G) | | | |
|---|---|---|---|---|---|
| Treatment | Pen No. | Body Weight Gain, g | % Increase | F/G | % Increase |
| Control | 241 | 173.50 | | 1.60 | |
| | 246 | 155.70 | | 1.68 | |
| | 249 | 152.60 | | 1.65 | |
| | 256 | 151.10 | | 1.61 | |
| | 259 | 157.22 | | 1.67 | |
| | 264 | 172.00 | | 1.53 | |
| Average | | 160.35[a] | — | 1.62[a] | — |
| Lasalocid 50 g/ton | 245 | 158.90 | | 1.52 | |
| | 248 | 141.17 | | 1.61 | |
| | 251 | 130.86 | | 1.68 | |
| | 254 | 184.70 | | 1.57 | |
| | 255 | 163.40 | | 1.63 | |
| | 262 | 130.63 | | 1.64 | |
| Average | | 151.61[a] | −5.5 | 1.61[a] | 0.4 |
| Zinc Bacitracin 50 g/ton | 244 | 227.33 | | 1.51 | |
| | 247 | 195.50 | | 1.56 | |
| | 250 | 236.33 | | 1.48 | |
| | 253 | 230.50 | | 1.61 | |
| | 258 | 229.60 | | 1.49 | |
| | 263 | 224.50 | | 1.60 | |
| Average | | 223.96[b] | 39.7 | 1.54[a,b] | 4.9 |
| Zinc Lasalocid 50 g/ton | 242 | 261.00 | | 1.54 | |
| | 243 | 208.33 | | 1.37 | |
| | 252 | 234.20 | | 1.56 | |
| | 257 | 240.60 | | 1.45 | |

TABLE 5-continued

| Treatment | Pen No. | Body Weight Gain, g | % Increase | F/G | % Increase |
|---|---|---|---|---|---|
| | 260 | 206.80 | | 1.50 | |
| | 261 | 251.50 | | 1.43 | |
| Average | | 233.74[b] | 45.8 | 1.48[b] | 8.6 |

MEAN having different superscripts are significantly different from the controls at the P <0.01 level of probability.

The data in Table 5 of Example IV show that the zinc complex of lasalocid is much superior to the sodium salt of lasalocid (Avatec) in promoting the growth of chicks and in increasing their feed efficiency.

EXAMPLE V

The zinc complex of lasalocid is purified by a purification process, incorporated into a pharmaceutical composition, and is then administered to dogs to stimulate their cardiovascular function.

Purification

To a liter of fermentation beer slurry containing zinc lasalocid which was produced in a manner as set forth in Example I, sufficient concentrated sulfuric acid is added to acidify the slurry of fermentation beer to a pH of about 3.0. The slurry is then mixed with about one liter of a butyl acetate organic solvent so that the zinc lasalocid is extracted in the solvent. The organic solvent which contains the lasalocid antibiotic is then separated from the acidic aqueous beer and is mixed with about one liter of an aqueous solution of sodium hydroxide having a pH of about 9.0 so that the lasalocid antibiotic will be extracted into the aqueous alkaline solution. Upon separation of the aqueous alkaline solution from the organic solvent, about one liter of methyl tertiary butyl acetate solvent is added to the aqueous solution to reextract the lasalocid antibiotic into the solvent. Thereafter, about 0.5 liter of methanol is first added to the solvent and then about 0.5 liter of a solution of zinc chloride in methanol is slowly added with vigorous agitation. A zinc complex of lasalocid is thereby formed in the methanol-solvent mixture which is subsequently filtered from the mixture, thoroughly washed with additional methanol and then dried. The formed zinc complex of lasalocid is suitable for administration to stimulate cardiovascular function.

Pharmaceutical Preparation

A pharmaceutical composition containing the zinc complex of lasalocid is prepared, the composition being suitable for parenteral administration.

The following ingredients are utilized to prepare a 5 ml. parenteral solution;

| zinc complex of lasalocid | 50 mg. |
|---|---|
| propylene glycol | 2.5 ml. |
| benzyl alcohol | 0.075 ml. |
| ethyl alcohol | 0.5 ml. |
| water | bal |

Treatment

The above parenteral composition, or any other form of the zinc complexes of the present invention, is administered to animals, e.g. mammals such as, for instance, dogs, prophylactically for, or having, a cardiovascular malfunction to stimulate their respective cardiovascular functions. The procedure utilized is similar to that set forth in U.S. Pat. No. 4,058,620 to Westley. The electrophysical and hemodynamic responses of the dogs are measured before and at various time intervals after intravenous injections of the composition. The parameters measured are myocardial force of contraction, heart rate and blood pressure. Positive inotropic effects are sought with minimal chronotropic effects being manifested in the treated animal.

EXAMPLE VI

A zinc complex of lasalocid as purified by the procedure of Example V is formulated into pharmaceutical tablets suitable for oral administration in stimulating cardiovascular function.

| zinc complex of lasalocid | 25 mg. |
|---|---|
| lactose | 113.5 mg. |
| corn starch | 55.5 mg. |
| pregelatinized corn starch | 8 mg. |
| calcium stearate | 3 mg. |

The tablets are made by thoroughly mixing the zinc complex, lactose, corn starch and pregelatinized corn starch, passing the mixture through a comminuting machine and then moistening the mixture with water in a mixer to produce a paste. The formed paste is screened to form granules and then dried. Calcium stearate is mixed with the dried granules and the granules compressed into tablets using a conventional tableting machine.

EXAMPLES VII-XIX

Other zinc complexes of polyether antibiotics are produced and recovered and the resultant complexes are used as coccidiostats and growth-promoting agents in poultry and as pharmaceutical formulations for myocardial stimulation in animals. The antibiotics utilized in the examples are monensin, nigericin, salinomycin, narasin, noboritomycin A & B, lysocellin, grisorixin, X-206, lonomycin, laidlomycin, SY-1, mutalomycin, and alborixin.

Each of the zinc complexes is produced and recovered by a process similar to that set forth in Example I except that the appropriate microorganism is utilized instead of the lasalocid producing microorganism. In accordance with the present invention, some of the recovered zinc complex of each antibiotic is utilized in a feed composition and fed to healthy and coccidiosis-infected groups of poultry while the remainder is purified in a process similar to that set forth in Example III. In accordance with the compositions and processes of the present invention, each of the zinc complexes, alone or in combination, is then administered to dogs to provide myocardial stimulation, or in treatment for coccidiosis in poultry, or for growth promotion in poultry. The uses for each of the zinc complexes are set forth below in tabular form, an "x" indicating that particular use.

TABLE 6

| Example Number | Polyether Antibiotic Zinc Complex | Poultry | | Myocardial Stimulation (Mammals) |
|---|---|---|---|---|
| | | Growth Promotion | Coccidiostatic Activity | |
| VII | Monensin | X | X | X |
| VIII | Laidlomycin | X | X | X |
| IX | Nigericin | X | X | X |
| X | Grisorixin | X | X | X |
| XI | Salinomycin | X | X | X |
| XII | Narasin | X | X | X |
| XIII | Lonomycin | X | X | X |
| XIV | X-206 | X | X | X |
| XV | Alborixin | X | X | X |
| XVI | SY-1 | X | X | X |
| XVII | Lysocellin | X | X | X |
| XVIII | Mutalomycin | X | X | X |
| XIX | Noboritomycin | X | X | X |

While the present invention has been described with reference to particular embodiments thereof, it will be understood that numerous modifications may be made by those skilled in the art without departing from the spirit and scope of the invention.

What is claimed is:

1. Zinc lysocellin.

2. A feed composition containing a nutrient and from about 75 grams per ton to 125 grams per ton of zinc lysocellin according to claim 1.

3. A feed additive composition consisting essentially of biomass recovered from a lysocellin containing fermentation broth made in accordance with the following steps:
   a) fermenting a fermentation broth inoculated with a Streptomyces microorganism capable of producing lysocellin by fermentation of the broth for a period of time and under suitable fermentation conditions in order to produce lysocellin in said fermentation broth; and
   b) providing in said lysocellin containing fermentation broth a water-soluble zinc salt in an amount sufficient to form a zinc complex of said lysocellin, which complex is insoluble in the fermentation broth.

4. A feed additive composition comprising at least about 5 percent by weight on a dry basis of a zinc complex of lysocellin.

5. A feed additive composition in accordance with claim 4 wherein the zinc complex comprises about 10 percent to about 50 percent by weight on a dry basis of the composition.

6. A biomass formed during fermentation of a lysocellin-producing microorganism, the biomass being comprised of dried mycelial material produced during fermentation of said microorganism, said biomass containing at least about 5% by weight of a zinc complex of lysocellin.

* * * * *